United States Patent [19]

Whiting et al.

[11] Patent Number: 5,163,753

[45] Date of Patent: Nov. 17, 1992

[54] DIFFERENTIAL THERMAL ANALYSIS CALORIMETER FOR THERMAL HAZARD TESTING

[75] Inventors: Lawrence F. Whiting; Stephen H. Humphrey, both of Midland, Mich.

[73] Assignee: The Dow Chemical Company, Midland, Mich.

[21] Appl. No.: 763,101

[22] Filed: Sep. 20, 1991

[51] Int. Cl.$^5$ .............................. G01N 25/00
[52] U.S. Cl. ............................ 374/010; 374/33; 374/40
[58] Field of Search ............... 374/10, 11, 12, 31, 374/40; 422/51

[56] References Cited

U.S. PATENT DOCUMENTS

| | | |
|---|---|---|
| 2,900,816 | 8/1959 | Anderson . |
| 3,491,581 | 1/1970 | Roberts et al. . |
| 3,524,340 | 8/1970 | Krakovetsky-Kocherzhinsky et al. . |
| 3,537,294 | 11/1970 | Stone . |
| 3,595,062 | 7/1971 | Stone . |
| 3,899,918 | 8/1975 | Privalov et al. . |
| 4,126,032 | 11/1977 | Ikeda et al. . |
| 4,333,332 | 1/1982 | Privalov . |

OTHER PUBLICATIONS

Selected pages from a book entitled "Thermal Analysis", Wesley Wm. Wendlandt, John Wiley & Sons, (1986).
Brochure and information from Fauske & Associates, Inc. entitled "RSST Reactive System Screening Tool", Burr Ridge, Ill., Mar. 1989.
Information from Systag, entitled "Laboratory Automation, Thermal Chemical Testing", Astra Scientific International, Inc., San Jose, CA. Oct. 16, 1989.
Various documents from Mettler Instrument Corporation including: "User friendly and expertly devised, these features characterize the RC1 software with which you control and monitor your processes, preprogrammed or interactively", Jan./1991; Innovative system conception perfect realization: your first and lasting impression of RC1 System technical concept. The modular structure combines the speed of interactive communication with the efficiency of distributed control to conduct intrinsically safe experiments, Jan./1991, 4 pages.
Article entitled "Thermal Hazard Evaluation by an Accelerating Rate Calorimeter", D. I. Townsend and J. C. Tou, Elsevier Scientific Publishing Company, Amsterdam, 1980.
"Process Safety", Chemical Engineering Progress magazine, selected articles and pages, Aug. 1985.
Article entitled "The Evaluation of Thermal Instabilities Using ARC and Advanced DTA Methods", by K. H. Mix, International Symposium on Runaway Reactions, Mar. 7-9, 1989, Cambridge, MA.
Various documents from Mettler Instrument corporation including: Product information bulletin "Four key analyses, one clear direction: Mettler analytical Instruments grow with your needs", 1989.
Brochure entitled Mettler, RC 1 Reaction Calorimeter; Product information bulletin "Mettler RC1 Reaction Calorimeter the Automatic Lab Reactor System".
Brochure entitled "Safety for your processes: your first objective"; 1791.
Product information bulletin "The calorimetric principle of the Mettler RC1", Jan. 1991.
Brochure "RC1 software".
Brochure "The precision tool for chemical research process development and systhesis: the Mettler RC1 Reaction Calorimeter", 1988.
Brochure RC1 System technical concept; brochure Flexible solutions to complex problems; and brochure for the Automation of Laboratory Syntheses: Mettler Contalab-The Intelligent Lab. Reactor 1990.
Brochure entitled Setaram from DSC 111 to TG-DSC 111, Astra Scientific International, Inc., San Jose, CA. Oct. 1989.
Brochure entitled Calorimeter C80D, Mixing and Reaction Calorimeter, Setaram, Astra Scientific International, Inc., San Jose, CA. Oct. 1989.
Paper entitled "Thermal Hazards Evaluation Using a New Multiple Sample Safety Calorimeter", by John D. Jones of Astra Scientific International, Inc. Sep. 27-30, 1987.

Primary Examiner—Daniel M. Yasich
Attorney, Agent, or Firm—Frost & Jacobs

[57] ABSTRACT

There is provided a differential thermal analysis calorimeter for performing thermal hazard testing procedures which can be utilized as an ancillary plug-in device with commercial thermal analysis data acquisition systems. Simultaneous measurement of heat flow of sample reactants and direct measurement of sample pressure is provided during a reaction within a substantially hollow furnace enclosure defining a heated zone having a heated top plate. A pair of longitudinally elongated heat conductive sample and reference tubes having upper and lower ends are each connected to the top plate adjacent their respective upper ends. The tubes depend downwardly from the top plate within the hollow furnace enclosure, and are heated by the heating means, whereby heat is conducted to the lower end of each tube longitudinally therealong. A pressure transducer is connected adjacent the upper end of the sample tube for directly measuring the pressure in the sample tube within the heated zone of the furnace.

23 Claims, 6 Drawing Sheets

DIFFERENTIAL THERMAL ANALYSIS CALORIMETER FOR THERMAL HAZARD TESTING

TECHNICAL FIELD

This invention relates to differential thermal analyzing devices such as for thermal hazard evaluations of reactive chemicals and evaluation of catalysts, and, more particularly, to an improved device which can be used as a plug-in module with commercial thermal analysis data acquisition systems to enable accurate and cost effective simultaneous measurement of heat flow and direct measurement of sample pressure during a reaction of chemical samples.

BACKGROUND ART

Calorimetry procedures are often performed on chemicals and mixtures of chemicals to evaluate thermal hazards and other safety concerns in chemical manufacturing, shipment, storage and handling procedures. Thermal instabilities and uncontrolled exothermic reactions can lead to a rapid release of energy which can manifest itself in cataclysmic explosions and other dangerous and destructive situations. Consequently, it is important to identify in advance as much information as possible about particular chemical reactions and related behavior of chemicals and mixtures of chemicals under various manufacturing, storage, and handling conditions.

Chemical reactions can be described by physical parameters such as temperature, pressure, concentration and time. Proper hazard assessment can be accomplished only when these parameters and the consequences of possible deviations of these parameters have been well investigated and determined. One of the safety hazards of most concern in the chemical industry is the thermal hazard, which is governed by the thermodynamics and chemical kinetics taking place in the often complex chemical reactions induced. For example, if there is an exothermic reaction taking place, the relative rate of heat production and resulting temperature range of heat build-up is critical. Additionally, if there is pressure build-up in the system, it is imperative that the vessel containing the chemicals be of sufficient strength and design to withstand maximum pressures and avoid rupture or other damage.

Various techniques have been devised to address these concerns. One such technique is known as Differential Scanning Calorimetry (DSC) in which the heat of reaction and various reaction kinetics can be evaluated. Conventional DSC techniques, however, are unable to measure pressure of the chemical reactants, and are generally poor at elucidating low activation energy or autocatalytic processes. In thermal hazard evaluation, reactions involving the release of gaseous products are often encountered. Conventional DSC devices often include standard aluminum sample pans which cannot withstand pressure build-up. Such pressure increase may damage or rupture the sample pans and/or the analyzer during the experiment, and further hampers the quantitative evaluation of the DSC data.

Another technique initially developed by the Dow Chemical Company is known as Accelerating Rate Calorimetry (ARC). The ARC technique comprises maintaining a sample in an adiabatic condition once an exothermic reaction is detected. In this way, the heat generated from the reaction will accelerate the reaction. While ARC techniques will obtain both pressure and thermal readings, the execution of the adiabatic requirement is very difficult, the equipment and experiments are expensive and difficult to maintain, and the testing requires several grams of sample to achieve the accuracy desired.

Conventional thermal analysis apparatus have generally utilized substantially solid furnace block elements to provide both support and heat to a sample vessel located therewithin. In these arrangements, a sample compartment or recess to receive a sample vessel is provided in a solid block of aluminum, silver, or similar material highly conductive of heat. Contact between the heated block and the sample compartment enables radial conduction of heat inwardly to the chemicals to be tested. Closely surrounding the sample compartment with a block of high thermal mass, however, tends to interfere with the sensitivity of the apparatus to temperature changes, thereby compromising the reliability and accuracy of the thermal analysis device.

A modified calorimeter device marketed by System Technik Ag. (Systag) under the trademark Radex contemplates supporting a sample vessel by way of a plurality of glass centering cylinders stacked upon one another within a cylindrical jacket heater. In this arrangement, a sample is to be warmed via thermal resistance (i.e., by air surrounding the sample vessel) by controlled heating of the jacket heater. The difference between the sample temperature and the cylindrical jacket temperature is monitored to provide thermal analysis results. Sensitivity to heat flow variations, and precise control of the thermal energy applied to the sample being tested, are consequently dependent upon the relatively low conductive qualities of air.

Another device known as the Reactive System Screening Tool (RSST) marketed by Fauske & Associates of Burr Ridge, Ill. is described as enabling the determination of heat flow data and pressure data at a relatively low price. However, the glass test cell of this device is designed as an open vessel, which makes pressure measurements on condensible samples virtually impossible. Pressure measurements are further obtained and analyzed by components located relatively remotely from the sample vessel itself, and a reference tube is not provided within the heated zone of the device.

Moreover, conventional thermal analysis equipment and processes contemplate stand-alone devices and/or equipment which is designed to operate substantially independently of other devices. For example, while some devices, such as the DSC 111 Transducer, from Setaram, of France, are described as being "complimentary" to conventional DSC analysis technology, they generally comprise stand-alone equipment which is not designed to be utilized as a "plug-in" module which can be readily used with commercially available data acquisition systems. Moreover, the DSC 111 measures pressure externally of the heated zone, is subject to condensation problems, and is relatively expensive. Similarly, while devices such as the RC1 Reaction Calorimeter System from Mettler Instrument (Hightstown, N.J.) include components described as "modular", these components are generally merely optional parts of an independently operated analysis arrangement.

Consequently, heretofore there has not been available a simple, inexpensive, reliable and accurate differential thermal analysis calorimeter which could readily be utilized as an ancillary plug-in device with commercially available thermal analysis data acquisition systems. Further, prior devices failed to provide a low cost, relatively simple arrangement which would enable accurate simultaneous measurement of heat flow of sample reactants and direct measurement of sample pressure during a reaction. Additionally, DSC type devices were limited to maximum sample sizes of about 50 mg, while ARC devices required at least several grams of sample for accurate results. Consequently, there was a gap in available technology, and a single device could not be used to handle a wide range of experiments.

DISCLOSURE OF THE INVENTION

It is an object of this invention to obviate the above-described problems and shortcomings of the previously available thermal analysis devices and processes in the industry.

It is another object of present invention to provide an improved, simple, and low cost Differential Thermal Analysis (DTA) calorimeter which enables reliable and accurate simultaneous measurement of heat flow data and direct measurement of sample pressure during a reaction.

It is yet another object of the present invention to provide a differential thermal analysis calorimeter featuring improved accuracy and reliability, and characterized by the utilization of a pair of longitudinally elongated heat conductive sample and reference tubes which are pendently spaced within a heated zone provided within a substantially hollow furnace enclosure.

It is also an object of the present invention to provide an improved calorimeter featuring a sample tube which depends downwardly from a heated portion of the furnace, having a pendent lower end within which a sample to be tested is placed and which is surrounded by substantially non-conductive gas.

It is also an object of the present invention to provide an improved calorimeter featuring a heat transfer or stabilization assembly attached in conductive arrangement with the sample tube to assist in heat transfer to the sample tube and to isolate the temperature gradient along the lower end of the sample tube.

It is another object of the present invention to provide an improved calorimeter whose structure facilitates the accurate determination of heat flow characteristics of a reaction simultaneously with the direct measurement of sample pressure within the heated zone of the device during the reaction.

It is yet another object of the present invention to provide a relatively low cost thermal analyzing device capable of detecting heats of reactions at lower temperatures (i.e., lower activation energy or autocatalytic processes) than those obtainable with conventional DSC techniques, and comparable to those obtained with ARC technology.

It is yet another object of the present invention to provide a substantially universal calorimeter which can be utilized in evaluating a wide variety of materials, and which can readily accommodate sample sizes ranging from milligrams to gram quantities.

In accordance with one aspect of the present invention, there is provided a differential thermal analysis calorimeter for performing thermal hazard testing procedures which can be utilized as an ancillary plug-in device with commercial thermal analysis data acquisition systems. This calorimeter enables simultaneous measurement of heat flow of sample reactants and direct measurement of sample pressure during a reaction, and includes a substantially hollow furnace enclosure defining a heated zone having a heated top plate. A pair of longitudinally elongated heat conductive sample and reference tubes having upper and lower ends are each connected adjacent the top plate at their respective upper ends. The tubes depend downwardly from the top plate within the hollow furnace enclosure, and are heated by the heating means, whereby heat is conducted to the lower end of each tube longitudinally therealong. At least the sample tube is to have a substantially hollow interior wherein sample reactants are received for reaction near the lower end. A pressure transducer is connected adjacent the upper end of the sample tube for directly measuring the pressure in the sample tube within the heated zone of the furnace.

In a preferred embodiment, temperature averaging sleeves are provided adjacent the lower ends of both the sample and reference tubes, and thermocouples monitor the heat flow conducted along such sleeves during a reaction. The calorimeter further preferably includes a heat transfer assembly conductively attached to the heated top plate and the sample and reference tubes above the lower ends of those tubes to assist in conductively transferring heat and to isolate the temperature gradient in the lower ends of the tubes.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
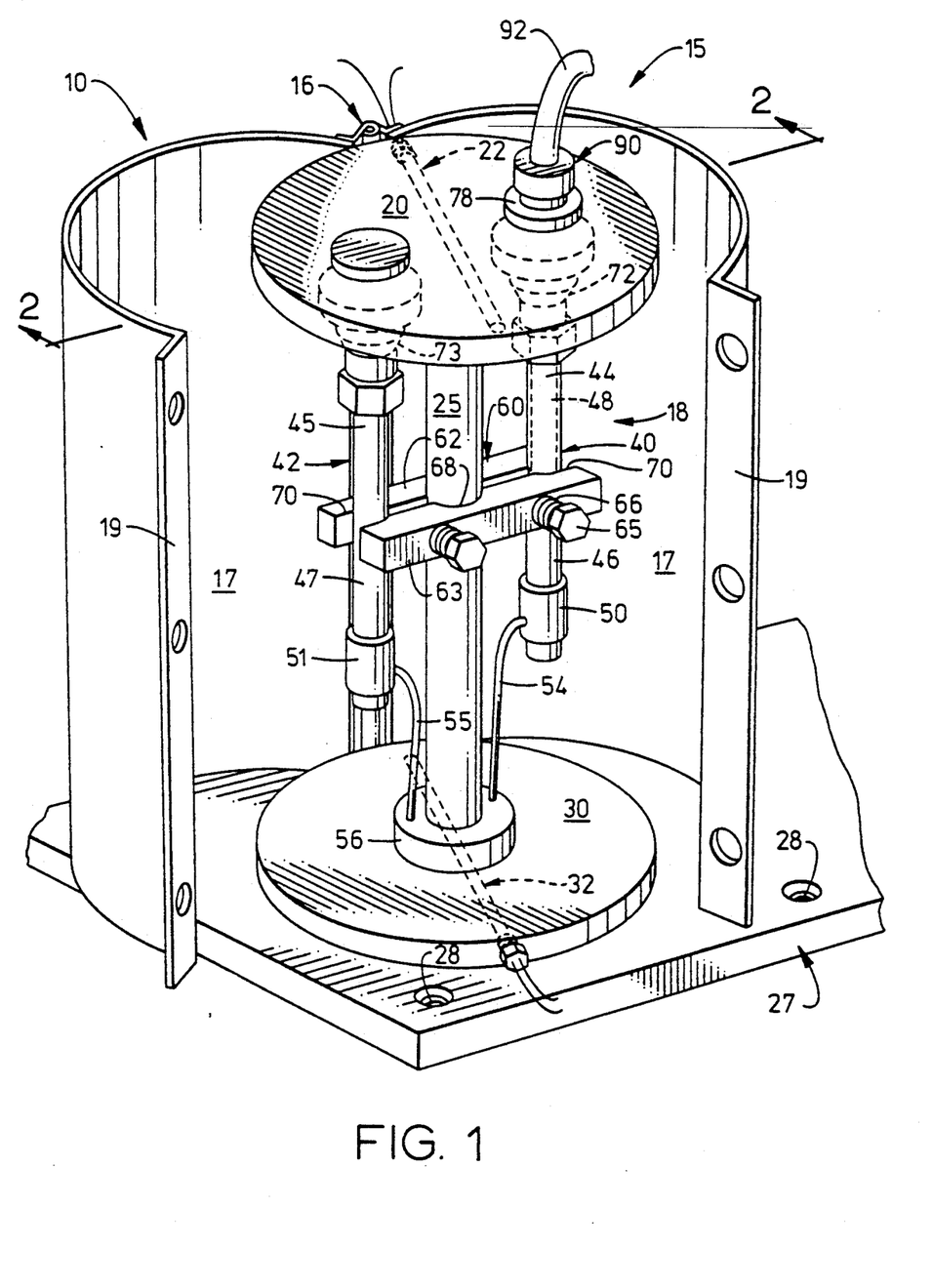
FIG. 1 is a perspective view of a differential thermal analysis type calorimeter made in accordance with the present invention.

Referring now to the drawings in detail, wherein like numerals indicate the same elements throughout the views, FIG. 1 is a perspective illustration of a macro-differential thermal analysis (Macro-DTA) calorimeter 10 made in accordance with the present invention. Calorimeter 10 is shown as including a substantially hollow furnace enclosure or "block" 15 which includes arcuate outer walls 17 in the form of door-like clamshell covers, which may be hingedly attached as shown or in a two piece arrangement hinged at the rear of the device and held closed by a bolted flange (e.g., 19).

Furnace 15 further includes a top plate 20, a bottom plate 30, and a substantially centrally located support post 25 extending between the top and bottom plates. Top and bottom plates 20 and 30, respectively, might preferably be provided in the form of heat conductive circular plates (e.g., stainless steel, constantan, nickel, Monel Metal ™ (an alloy such as sold in the industry comprising of 67% nickel, 28% copper and 5% other elements), or aluminum plates) about one-half inch in thickness and about 5 inches in diameter. Support post 25 is also preferably provided of relatively highly conductive material such as stainless steel or aluminum, and, in a preferred embodiment, is about one inch in diameter.

Figure 2:
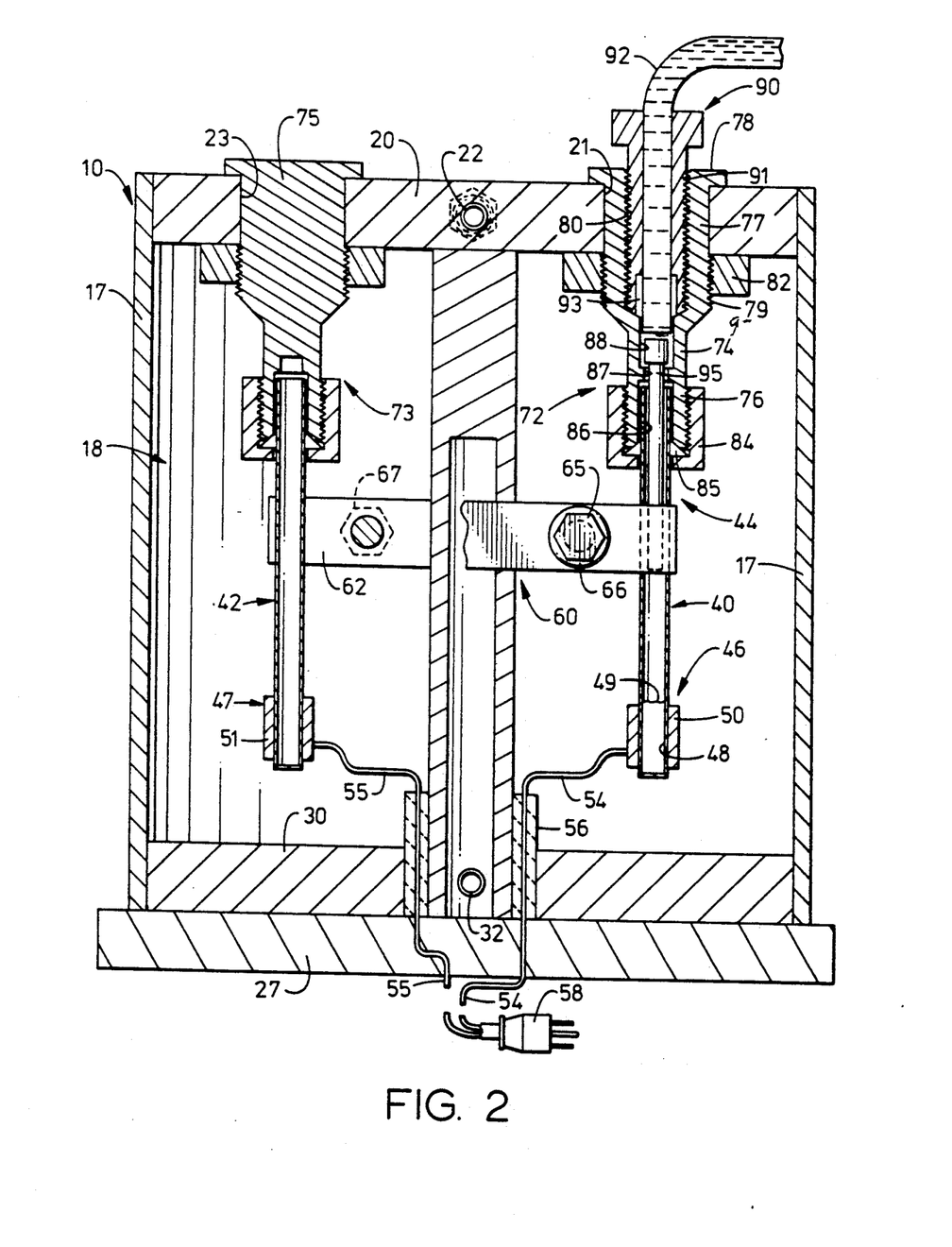
FIG. 2 is a vertical cross-sectional view of the calorimeter of FIG. 1.

As illustrated in FIGS. 1 and 2, top plate 20 may be heated by an internal, cartridge type heater 22 or similar means for selectively elevating the temperature thereof. Alternately, the top plate 20 can be heated indirectly, e.g., by conduction of heat from a heater placed elsewhere. As will be understood, bottom plate 30 may also be provided with similar means 32 for heating plate 30. Outer walls or covers 17, and top and bottom plates 20 and 30 serve to define a heated zone 18 within calorimeter 10. Particularly, walls 17 are articulated along longitudinal hinge 16 to provide easy access to the interior of furnace 15, and can be locked closed such as via bolting flanges 19.

A safety shield (not shown) is preferably provided about the outer periphery of calorimeter 10 to provide an explosion shield enclosing the entire device. This shield can be constructed of stainless steel plate or similar high strength, corrosion resistant material (e.g., approximately one-eighth inch in thickness). The shield might be provided as a "hinged can" or clam shell design similar to the outer walls 17, secured in a hinged manner at the back of the calorimeter 10 and lockable in closed condition by a plurality of bolts in the front. The safety shield might typically be 10" in diameter where the curved outer walls 17 of calorimeter 10 are about 5 inches in diameter, and the space between the shield and the outer walls should typically be filled with appropriate thermal insulation. Such shield is provided to contain all pieces of calorimeter 10 and sample materials in the event of a catastrophic explosion or similar sudden release of energy.

As seen in FIG. 1, calorimeter 10 is illustrated as being mounted on a stand 27 which is preferred to thermally isolate calorimeter 10 from other thermal analysis and/or data acquisition components with which the present invention can be utilized. Stand 27 might further secured (e.g., such as via bolts 28) to other components or onto a mounting device to provide stability, as appropriate.

A pair of longitudinally elongated heat conductive sample and reference tubes 40 and 42, respectively, are provided in spaced relationship within heated zone 18. Particularly, sample tube includes an upper end 44 and lower end 46 while reference tube 42 features corresponding upper end 45 and lower end 47. Sample tube 40 is secured to upper plate 20 adjacent its upper end 44 by means of a compression fitting 72. Compression fitting 72 preferably further includes an elongated tubular member 74 which features a lower threaded tubular end 76, and an upper enlarged end 77 with an upper outwardly extending flange 78 and external threads 79 spaced downwardly therefrom.

As will be understood, compression fitting 72 is mounted within aperture 21 of top plate 20, and may be held therewithin by its upper flange 78, and a lock nut 82 threaded onto external thread 79 as indicated. The lower end of compression fitting 72 includes an internal recess 86 designed to sealingly receive the upper end 44 of sample tube 40, and a compression nut 84 engages external threads 76 and compression ring 85 to sealingly engage sample tube 40. A stop lip 87 is further shown to facilitate proper alignment and sealing of tube 40 within recess 86.

Means 90 for directly measuring the pressure of sample reactants within sample tube 40 is connected adjacent the upper end of tube 40, preferably within a portion of compression fitting 72 as illustrated. Particularly, a pressure transducer 90, such as the Model PT435A-1.0M-T16 available from Dynisco of Norwood, Mass., is illustrated as comprising external threads 91 which engage internal threads 80 formed within the central recess of compression fitting 72.

Transducer 90 includes a probe 93 extending at least partially into the heated zone 18 of calorimeter 10, and which may, in some instances, extend into the upper end 44 of tube 40. The Dynisco transducer was chosen as a 1000 psig full scale transducer constructed of 316 stainless steel, which provides a liquid filled sensing head (e.g., probe 93) mounted in the heated zone 18 as discussed. Other corrosion resistant materials (e.g., Hastelloy C-276, as available from Omega Engineering Inc. of Stamford, Conn.) could alternately be utilized in probe 93.

As seen in FIG. 2, probe 93 is sealingly received adjacent upper recess 88, thereby effectively defining the upper limit of the inner volume V of tube 40 and recess 86. This arrangement allows direct measurement of sample pressure at a substantially constant volume (V) and in an environment of stable temperature which effectively eliminates any "cold spots" where condensible gases may accumulate and compromise the accuracy of the pressure measurements. Moreover, the entire volume of the sample tube 40 is located within heated zone 18 of calorimeter 10, and by locating pressure transducer 90 in an arrangement directly and intimately attached to furnace block 15, wherein the pressure monitoring means extends at least partially into the heated zone thereof, most accurate data can be obtained.

The sample pressure may be transmitted via a sealed, mercury filled pressure transmitting line 92 to an appropriate strain gauge or other pressure sensing apparatus. Particularly, pressure transmitting line 92 would preferably comprise a capillary tube filled with mercury and sealed at its opposite ends by pressure sensitive diaphragms. Pressure changes within the constant volume (e.g., V) of sample tube 40 and recess 86 caused by chemical reactivity causes deflection of the diaphragm (e.g., diaphragm 97 in FIG. 2) adjacent transducer 90, and that deflection is transmitted through the substantially incompressible mercury in line 92 to an oppositely disposed diaphragm (not shown) on line 92. In this way, no material (e.g., atmosphere above the sample in tube 40 and recess 86) is permitted to exit heated zone 18, and accurate pressure readings are obtained within a substantially constant volume.

As illustrated in FIG. 2, an inert pressure insert 95 (e.g., stainless steel or other inert material) might also preferably be extended from the upper portions 88 of recess 86 into the upper end 44 of tube 40. This pressure insert is contemplated for reducing the head space or volume V above the sample within the sample tube 40, thereby increasing the observable sensitivity of pressure changes therewithin for non-condensible gases formed during reaction.

At the lower ends 46 and 47, of sample and reference tubes 40 and 42, respectively, heat averaging sleeves 50 and 51 are preferably arranged to monitor heat flow. Heat averaging sleeves 50 and 51 can be provided in the form of a thin cylindrical sheath of brass, nickel, or other oxidation resistant material, and can be useful in attaching and holding the contact (such as through a silver soldered connection) for means (e.g., 54 and 55) for monitoring temperature changes during a reaction. The means for monitoring temperature changes can be provided in the form of type K thermocouples of approximately 0.010" (0.025 cm) in diameter, as commonly available in the industry such as from Omega Engineering of Stamford, Conn., or other thermocouple, differential thermocouple, thermopile, thermistor, or resistance thermometer types as needed to match particular data acquisition systems.

Thermocouples 54 and 55 can be connected through bottom plate 30 through a ceramic insulator 56 for connection with a standard connector (e.g., a 15 pin connector) 58 for quick connection with commercially available data acquisition devices (e.g., a DuPont DSC 910 Cell base). Connector 58 may also provide a plug-in type connection for various other data control lines to and from calorimeter 10, to provide power to heaters 22 and 32, the differential heat flow signal along with the reference thermocouple (55) and sample thermocouple (54) signals, and the like. Similarly, the output from pressure transmitting line 92 and pressure transducer 90 can be connected in a similar fashion to commercially available data acquisition equipment, such as the signal B port of a 1090 thermal analyzer as available from TA Instruments, New Castle, Del.

As illustrated in FIGS. 1 and 2, reference tube 42 is similarly attached in depending fashion from top plate 20 via a compression fitting 73. As it is contemplated that reference tube 42 will not contain samples to be tested, no pressure monitoring means need be provided with compression fitting 73, and a plug 75 or blank compression fitting can be used, as illustrated. As will be understood, heat from heater 22 and/or heater 32, will be conductively transferred through compression fittings 72 and 73 and downwardly through sample tube 40 and reference tube 42, respectively. Due to the relatively lower conductive nature of the air surrounding the lower ends of pendent tubes 40 and 42, little or no heat will be transferred within heated zone 18 except via direct conduction between adjacent parts.

In a preferred example, the sample and reference tubes can be provided as closed end tubes having an outside diameter of approximately 0.25 inches, approximately 3 inches in length, and made of stainless steel or Hastelloy C-276.

A heat transfer assembly 60 is also preferably provided within furnace block 15 to facilitate efficient conduction of heat therewithin, and to minimize the temperature gradient along the upper end 44 of sample tube 40 to provide for more stable and accurate pressure measurements. Heat transfer assembly 60 is illustrated as including a pair of oppositely disposed clamp arms 62 and 63 connected by at least one biasing means (e.g., spring-loaded clamp bolts) 65. Particularly, the corresponding clamp arms 62 and 63 include a central collar portion 68 for frictionally fitting around the outer portions of support post 25 at a position spaced between top and bottom plates 20 and 30, and having oppositely disposed cut-out end portions 70 for adjustably receiving the respective sample and reference tubes 40 and 42. Cut-out portions 70 preferably conform closely to and at least partially enclose the outer periphery of the tubes in order to provide connective support and good thermal conductivity.

Clamp bolts 65 preferably each include a compression spring 66 on one side, and a nut 67 on the other side. Springs 66 enable clamp bolts 65 to be tightened sufficiently to provide frictional attachment of heat transfer assembly 60 at a predetermined longitudinal position along support post 25, while allowing a predetermined amount of lateral adjustability therebetween to accommodate insertion and removal of sample and reference tubes 40 and 42 without having to loosen bolts 65. In this way, a "snap fit" of tubes 40 and 42 is provided between clamp arms 62 and 63, thereby facilitating insertion and removal of the tubes as desired.

Heat transfer assembly 60 also provides good thermal contact between support post 25 and tubes 40 and 42, improving the base line linearity and reducing undesirable error or "noise" of the monitored heat flow along the tubes. Consequently, a properly designed heat transfer assembly 60 can simplify and facilitate insertion/removal procedures for the sample and reference tubes, and can further augment the reliability and accuracy of calorimeter 10. The means for heating can be conveniently located adjacent to or within either top or bottom plates (20, 30), or both. Particularly, heat transfer assembly 60 provides an additional conduction path for movement of heat from a means for heating (e.g. heater 22 and/or heater 32) to tubes 40 and 42. It has also been observed that heat transfer assembly 60 also helps to stabilize the temperature along tubes 40 and 42 and minimize the temperature gradient along the upper ends (e.g., 44 and 45) of the tubes between assembly 60 and top plate 20. Stabilizing the temperature in the upper portions of sample tube 42 facilitates the maintenance of stable conditions therewithin, allowing more accurate and reliable pressure monitoring by transducer 90.

As can be appreciated, where heat transfer assembly 60 is utilized, the upper ends (44 and 45) of the tubes will thereby be heated substantially uniformly along their longitudinal length, and the lower ends (46 and 47, respectively) will have a temperature gradient as heat is conducted longitudinally downwardly from top plate 20 and upwardly and downwardly from assembly 60. The pendent nature of lower ends 46 and 47, and the requirement that heat energy be transferred longitudinally along the tube walls, effectively isolates lower ends 46 and 47 from extraneous heat and heat absorbing structures, and facilitates accurate monitoring of heat flow via thermocouples (e.g., 54 and 55). Each tube is thereby provided as a unitary and convenient structure which is effectively longitudinally subdivided in use to enable optimum and simultaneous measurement of heat flow data and direct sensing of pressure changes due to chemical reactions.

For optimum performance, it is preferred that sample and reference tubes 40 and 42 be provided with substantially identical length, material, and mass. While only sample tube 40 is required to have a hollow interior (e.g., 48), it is preferred that both tubes have substantially identical physical characteristics to insure maximum linearity and reliability of heat flow results. Heat averaging sleeves 50 and 51 might be provided as open ended tubes made from stainless steel brass, nickel or other conductive material, approximately 0.01" (0.025 cm) thick and about 0.75" (1.9 cm) in length, and can conveniently be split along one longitudinal side to facilitate a flexible but snug fit over tubes 40 and 42, respectively. Tubes 40 and 42 might also be fitted with glass liners or inserts for handling particularly corrosive reactants, and might be disposable in nature.

Figure 3:
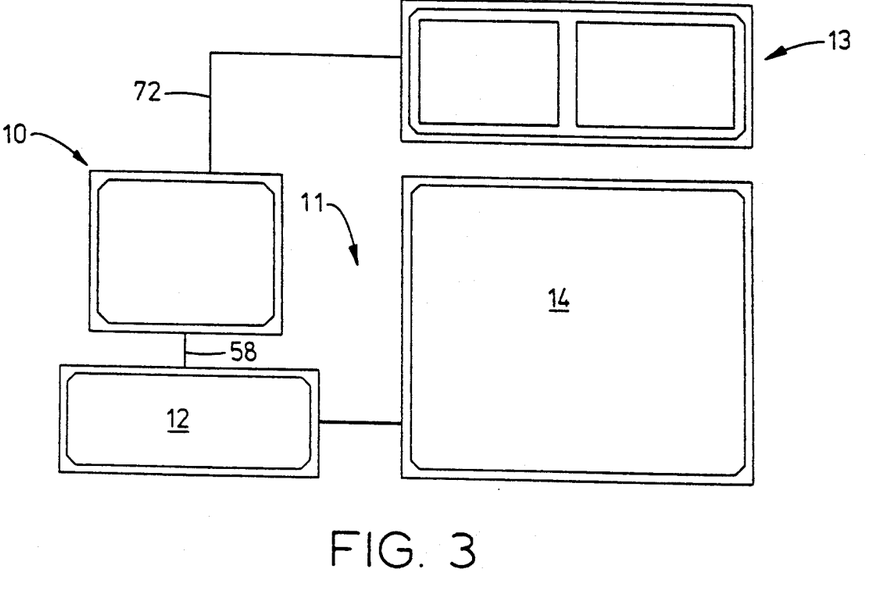
FIG. 3 is a schematic illustration of a typical plug-in arrangement of a differential thermal analysis calorimeter of the present invention with commercially available data acquisition equipment.

As mentioned above, the differential thermal analysis calorimeter 10 of the present invention can be readily utilized in a plug-in modular arrangement in conjunction with various commercially available data acquisition devices. FIG. 3 illustrates schematically how a calorimeter 10 made in accordance with the present invention might be conveniently "plugged in" with a conventional thermal analysis data acquisition system 11 (e.g., a DuPont Model 1090 analyzer). In particular, the subject calorimeter 10 might be mounted on a cell base 12 and connected thereto via a standard 15 pin plug (e.g., 58), as mentioned above. Similarly, the means (e.g., 90) for monitoring pressure can be connected via line 72 to a pressure data acquisition device 13. Particular connections (e.g., which pins to attach to particular input/output plugs or modules) would, of course, have to be determined based on the particular system(s) contemplated. A programmer/controller 14 would conventionally supervise the operations of both cell base 12 and pressure data acquisition device 13, and implement appropriate analysis of the test results.

Figure 4:
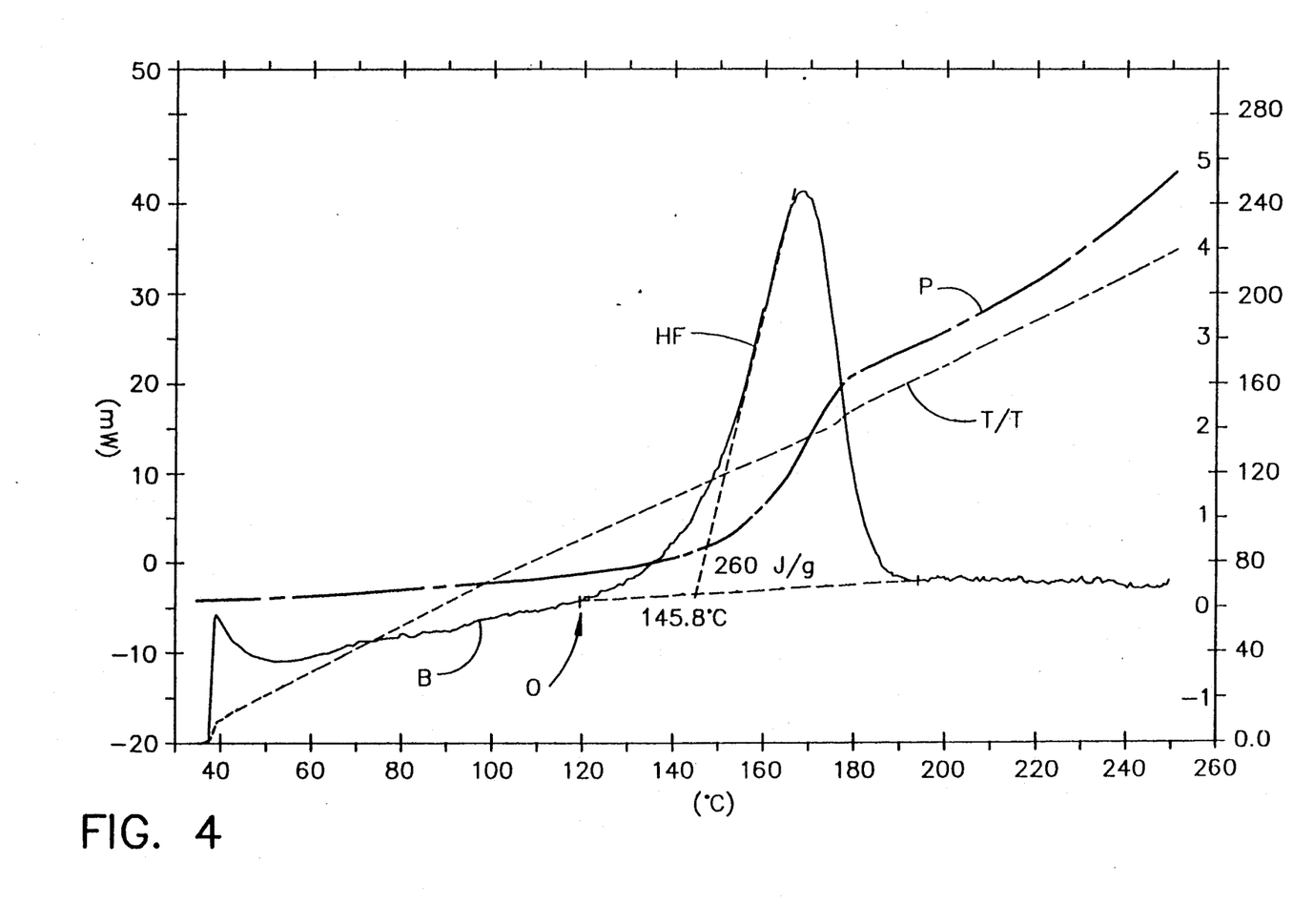
FIG. 4 is a graphical representation of typical heat flow curves illustrating temperature and pressure variations during a hazard analysis of the decomposition of a tBu$_2$O$_2$ sample.

Experiments were undertaken to determine the precision of the subject Macro-DTA calorimeter to determine the effect of undersized or oversized sample quantities on the test measurements, measurement changes associated with varying scan rates in the calorimeter, and to compare the accuracy of the subject calorimeter with available DSC and ARC equipment. These experiments recorded the onset temperature of the exothermic reaction (temperature at which the reaction was detected), total heat flow, and total pressure rise of the reaction. FIG. 4 illustrates a graphical representation of a typical set of heat flow, temperature and pressure curves from a hazard analysis test using a 20% solution of tert-butyl peroxide ($tBu_2O_2$) in toluene solvent as a decomposition standard. The $tBu_2O_2$ was obtained from Aldrich Chemical of Milwaukee, Wis.

Before performing the experiments, the Macro-DTA calorimeter was calibrated by running melting point calibration tests on pure samples of lead, tin, biphenyl and either indium or benzoic acid standards. Additionally, the pressure measurement functions were checked with water before each set of measurements, wherein a tube containing deionized water was run in the instrument, and the values from the pressure baseline were subtracted from the raw water vapor pressure measurements. These corrected vapor pressures were then compared to literature values, and resulting pressure measurements were deemed acceptable if found to be accurate within 10 psi and precise within 2 psi (using the Dynisco transducer). Generally, all such tests were performed at a scanning rate of one degree centigrade per minute (° C./min), except during the experiments to identify variations due to scan rate changes.

As illustrated in FIG. 4, the reaction onset temperature (O) was determined to be the point at which the heat flow (HF) due to the process or reaction exceeded the baseline or noise level (B) by about three times the standard baseline noise level. The total heat of the experiment was determined as the integrated area underneath the heat flow curve HF. The stoichiometric ratio of the gaseous products of the initial reactant was calculated from the total pressure rise. The molar equivalent of the gases formed from the decomposition was calculated by assuming that the pressure rise was the sum of the vapor pressure of the solution and the reaction products, that the vapor pressure of the solvent obeyed Raoult's Law, and that the gaseous reaction products acted ideally. For each experiment, the sample was loaded into sample tube 40 either by a syringe or, if solid, by simply dropping inside the tube. The scanning rate is also shown in FIG. 4 as the temperature versus time (T/T) sloping line.

With regard to the precision measurements, the standard deviation found with regard to the onset temperature O was about 1° C., and the relative standard deviation of the total heat was about 2%. The measured heat of reaction for $tBu_2O_2$ was in excellent agreement with previous measurements of about 1.23 kJ/g.

A second set of experiments measured the heat flow and pressure rise for both undersized and oversized $tBu_2O_2$ samples. For comparison, "properly" sized (or proper size) samples were defined as an amount sufficient to substantially fill the sample tube to the top of the temperature averaging sleeve (e.g., 50). In this regard, undersized samples were about 50% smaller than proper size, and oversized samples were about 50% larger. Experiments with the undersized samples resulted in a heat of reaction which was within the 90% confidence interval of the heat of reaction determined in the properly sized sample. The onset temperature and the product to reactant ratio were both slightly higher than those of the properly sized samples.

Similarly, results of measurements taken with oversized samples revealed both onset temperature and product to reactant ratios within the 90% confidence interval, although the heat of reaction was smaller than the same measurements taken on the properly sized sample (although this difference was less than 8%). Overall, the differences between measurements obtained with the differing sizes of samples were quite small, and it was concluded that sample size had little noticeable effect on the critical measurements.

A third set of experiments was performed wherein the scanning rate of the Macro-DTA calorimeter was varied between 0.5° C./min., 1° C./min., and 2° C./min. The results of these measurements performed on the decomposition of $tBu_2O_2$ at different scan rates produced the follow results:

| scan rate (°C./min) (T/T) | mass $tBu_2O_2$ (mg) | heat | | pressure | |
|---|---|---|---|---|---|
| | | $T_{onset}$ (°C.) (O) | $\Delta H$ (kJ/g) | $P_{tot}$ (200° C.) (psi) (P) | $n_{prod}/n_{react}$ |
| 0.5 | 38.1 | 125 | 1.44 | 312 | 0.95 |
| 1 | 37.0 | 128 | 1.43 | 294 | 0.90 |

Table: Macro-DTA Measurements on the Decomposition of $tBu_2O_2$ at Different Scan Rates -continued Macro-DTA Measurements on the Decomposition of $tBu_2O_2$ at Different Scan Rates

| scan rate (°C./min) (T/T) | mass $tBu_2O_2$ (mg) | heat $T_{onset}$ (°C.) (O) | ΔH (kJ/g) | pressure $P_{tot}$ (200° C.) (psi) (P) | $n_{prod}/n_{react}$ |
|---|---|---|---|---|---|
| 2 | 38.7 | 137 | 1.39 | 323 | 0.98 |

Wherein $n_{prod}/n_{react}$ is the product to reactant molar ratio calculated assuming $V_{headspace} = 0.65$ ml The maximum difference observed between any two of the temperature and pressure curves of these experiments was about 5%, and the variations in enthalpy calibration curves showed no obvious relationship to the changes in the scan rates. It was noticed that onset temperatures (O) for the decomposition measurements increased slightly with the faster scan rates (T/T), but otherwise the data from decomposition measurements showed no discernible relationship to changes in the scan rate. Similarly, the pressure data showed no discernible correlation to variations in the scan rate. While the heat of reaction seemed to decrease slightly as the scan rate increased, those changes were comparable to the experimental random error observed.

Additionally, while there remained some unaccountable specific differences in the observed experimental values as the scan rate was varied, the present calorimeter provided substantially accurate data which was relatively unaffected by variations in the scan rate. The results also showed that measurements of the onset temperatures 0 made with the Macro-DTA device fit the generally accepted pattern of lower onset temperatures with lower scan rates.

The fourth set of experiments undertaken compared similar measurements from conventional DSC and ARC devices with measurements from the subject Macro-DTA calorimeter based upon decomposition of (a) $tBu_2O_2$, (b) 2.2'—azobis—2-methylpropionitrile (AIBN) and (c) styrene. The DSC device used was manufactured by Polymer Laboratories of Mudelein, Ill., and was operated from the ATvantage System with a DuPont DSC 910 cell base and the DSC cell as a calorimeter (version 4.3 software). The ARC device was manufactured by Columbia Scientific Industries of Austin, Tex.

Figure 5:
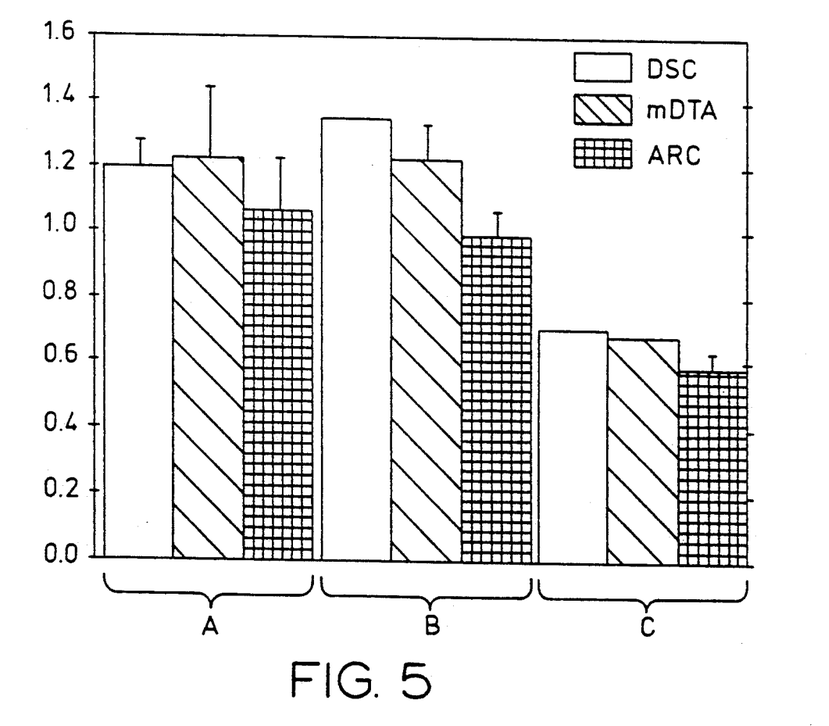
FIG. 5 is a graphical comparison of the heat of reaction (illustrated on the vertical axis in kJ/g) of samples of tBu$_2$O$_2$, AIBN, and styrene as determined via conventional DSC, ARC and differential thermal analysis calorimeter of the present invention, respectively.

FIG. 5 illustrates results of the comparison between the heats of reaction for (a) the 20% $tBu_2O_2$ in toluene solution; (b) a 12% AIBN in $CH_2Cl_2$ solution; and (c) styrene samples. The Macro-DTA calorimeter results are shown as the middle bar in each of the three examples, with the DSC results illustrated to the left, and the ARC results to the right. The measured heats of reaction for each of the three test materials are in reasonable agreement with published values reported in the literature (i.e, 1.23 kJ/g for $tBu_2O_2$, 1.39 kJ/g for AIBN, and 0.68 kJ/g for styrene). These results illustrate that the subject calorimeter measured the heat from each of these three reactions quantitatively, while the pressure data from these experiments illustrated that the pressure increases due to decomposition of $tBu_2O_2$ and AIBN in the subject Macro-DTA device were comparable to those in the ARC device (of course, the DSC device has no pressure measurement capability). Furthermore, when head space volume to sample volume ratios were taken into account, the pressure data from the subject calorimeter agreed closely with the pressure rises observed with the ARC device.

Figure 6:
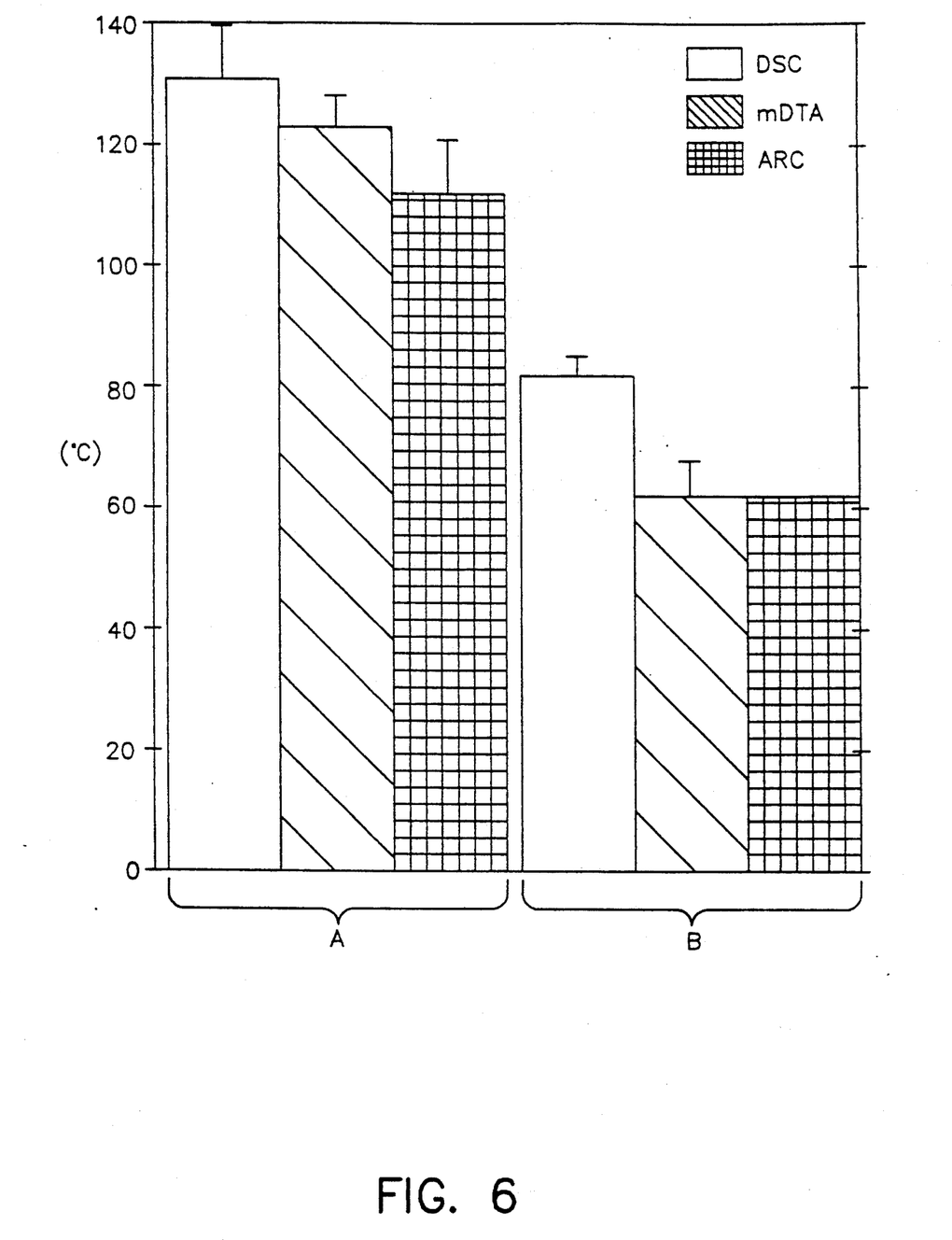
FIG. 6 is a graphical comparison of the detected onset temperatures of the decomposition of samples of tBu$_2$O$_2$ and AIBN determined via conventional DSC and ARC processes, as well as the differential thermal analysis calorimeter of the present invention.

FIG. 6 shows the results of a comparison between the onset temperatures (O) of: (a) the 20% $tBu_2O_2$ solution; and (b) the 12% AIBN solution samples. Again, results observed with the Macro-DTA device are shown by the center bar of each comparison, while results from the DSC device are shown to the left, and results from the ARC device are shown to the right. These results illustrate that the observed onset temperature of reactions in the Macro-DTA device were less than those observed with the DSC device, and slightly greater than (with regard to $tBu_2O_2$) and equal to (for AIBN) to those obtained with the ARC device.

The onset temperatures from styrene experiments were not compared because of the differences in concentrations of inhibitor, and ratios of sample volume to oxygen in the headspace. All of these parameters directly affect the detected onset temperatures for styrene polymerization, and would, therefore, influence comparison results. The compared onset temperatures, however, showed that the Macro-DTA results agreed closely with those measured in the other two instruments.

The results of the various experiments discussed above demonstrate that the present invention can obtain measurements of temperature, heat flow, and pressure, as good as, and in many cases better than, the results achieved with available DSC and ARC technology. Pressure increases observed were found to agree well with results obtained in the ARC devices, and detected onset temperatures of a reaction fall between those of the DSC and ARC devices. Scan rates and sample size exhibit no appreciable effect on the heat flow results within the ranges tested, and heats of reaction measured on the DSC, ARC, and subject Macro-DTA device agree within acceptable ranges of error for thermal hazard evaluation for all materials tested.

Consequently, the subject instrument is capable of accurate and precise measurement of heat flow of reaction simultaneously with direct measurement of the pressure of the sample. The subject device further detects onset temperatures of reactions at lower activation energies and temperatures than those obtainable in conventional DSC devices, and approaches those observed in using ARC technology. The present device is also equally applicable to evaluate gas/solid, gas/liquid, high pressure liquid/solid, and liquid/liquid reactions. More importantly, the structure of the subject device is quite simple in construction, easy to manufacture, repair and maintain, relatively inexpensive, and capable of immediate and rapid installation in conjunction with commercially available data acquisition equipment. The structure of the present invention also enables application of a more predictable constant temperature heating rate, allowing tests to be completed more quickly than with ARC devices.

Figure 7:
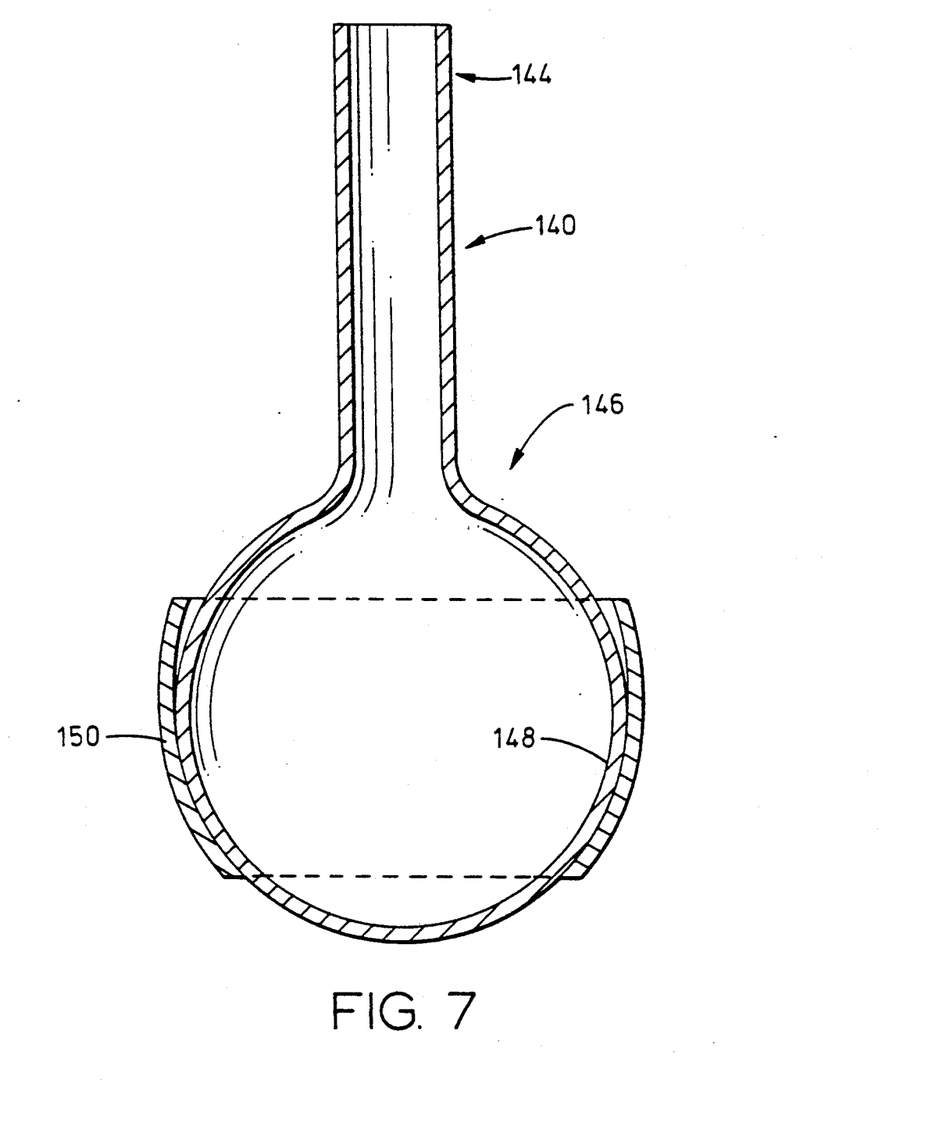
FIG. 7 is a vertical cross-sectional view of an alternate embodiment of sample and reference tubes which can be utilized in the subject calorimeter of the present invention to accommodate various sample sizes.

FIG. 7 illustrates an alternate sample tube 140 similar to the sample and reference tubes 40 and 42 described above. Tube 140, however, comprises an enlarged lower end 46 in the form of a hollow sphere, and illustrates merely a sample of the myriad of tube structures which can be used to accommodate the dynamic range of sample sizes which can be equally evaluated with the present Macro-DTA calorimeter. Sample tube 140 preferably includes a tubular upper end 144 having substantially the same conformation as tubes 40 and 42 discussed above, for easy substitution therefore in conjunction with calorimeter 10. Larger sample size capacity can be advantageous in more accurate evaluation of, for example, heterogeneous materials.

It is contemplated that tube 140, and a matching reference tube 142 (not shown), would simply attach to compression fittings 72 and 73 and clamp arms 62 and 63 of the heat transfer assembly for insertion/removal, as described above. A modified heat averaging sleeve 150 might further be provided with tube 140 for quick connection with thermocouple 54. Recalibration of calorimeter 10 will most likely be required initially when sample and reference tubes of different sizes are interchanged, in order to insure optimal accuracy and reliability, however, this function could be preprogrammed into the control system. In this way, the structure of calorimeter 10 can be quickly and conveniently adapted to accommodate a large variety of sample sizes, from milligram to gram quantities, thereby providing a single instrument able to accommodate an wide range of evaluation tasks in a simple and reliable manner.

Having shown and described the preferred embodiments of the present invention, further adaptions of the Macro-DTA thermal analysis calorimeter described herein can be accomplished by appropriate modifications by one of ordinary skill in the art without departing from the scope of the present invention. Several of the potential modifications have been mentioned, and others will be apparent to those skilled in the art.

For example, in appropriate applications, the sample tube (e.g., 40) of the present invention could be fitted with structure to enable automatic placement or shot addition of samples, as well as with appropriate mixing or stirring structure to assist in simulating desired conditions for proper hazard analysis. Similarly, in most applications, appropriate safety releases or cutouts will most likely be included in the Macro-DTA design in order to protect the equipment from exceeding its maximum safe operating temperatures and pressures.

It will be understood that the present Macro-DTA device could also be easily modified to analyze reactions at constant elevated or reduced pressure or continuous gas flow, such as by fitting additional inlet/outlet arrangement(s) relative to the recess (e.g., 86) of the compression fitting (e.g., 72). Similarly the present calorimeter could be configured to maintain the sample and reference tubes at either highly elevated or lowered temperatures for appropriate evaluation procedures. Another modification might comprise providing additional compression fittings and, a heat transfer assembly having additional cutout portions to receive additional sample tubes in order to accommodate multiple samples simultaneously.

Accordingly, the scope of the present invention should be considered in terms of the following claims and is understood not to be limited to the details of structure and operation shown and described in the specification and drawings.

We claim:

1. A differential thermal analysis type calorimeter for performing thermal hazard testing procedures which can be utilized as an ancillary plug-in device with commercial thermal analysis data acquisition systems, and which enables simultaneous measurement of heat flow of sample reactants and direct measurement of sample pressure during a reaction, said calorimeter comprising:
a substantially hollow furnace enclosure defining a heated zone having a top plate, and means for heating said top plate;
a pair of longitudinally elongated heat conductive sample and reference tubes having upper and lower ends, said tubes each connected to said top plate adjacent their respective upper ends and depending downwardly therefrom within said hollow furnace enclosure, whereby said tubes are heated by said heating means and said top plate via conduction to said lower end of each tube longitudinally along said sample tube, said sample tube having a substantially hollow interior adjacent said lower end wherein sample reactants are received for reaction;
means for directly measuring the pressure of said sample reactants within said sample tube, said pressure measuring means sealingly attached adjacent the upper end of said sample tube and extending at least partially into said heated zone; and
means for monitoring the heat flow conducted along said sample and reference tubes, respectively, during a reaction.

2. The calorimeter of claim 1, further comprising a heat transfer assembly conductively attached to said heating means and said sample and reference tubes above their respective lower ends.

3. The calorimeter of claim 2, wherein said furnace enclosure further comprises a bottom plate, and a longitudinal support post which spans between said top and bottom plates within said enclosure, and wherein said heat transfer assembly is supported along said support post.

4. The calorimeter of claim 2, wherein said upper end of said sample tube is mounted between said top plate and said heat transfer assembly and is heated by conduction from connection to said top plate and said heat transfer assembly such that substantially no temperature gradient is produced therealong.

5. The calorimeter of claim 3, wherein said heat transfer assembly comprises oppositely disposed clamping arms to adjustably receive said sample and reference tubes in spaced relationship within said furnace enclosure.

6. The calorimeter of claim 5, wherein said clamping arms further comprise a biasing means for providing automatically adjustable connections for receiving and supporting said sample and reference tubes.

7. The calorimeter of claim 1, further comprising output means for selectively connecting said pressure measuring means and said heat flow monitoring means to thermal analysis data acquisition equipment.

8. The calorimeter of claim 1, wherein said means for directly measuring the pressure of said sample reactants comprises a pressure transducer having a probe located adjacent said upper end of said sample tube.

9. The calorimeter of claim 1, wherein said means for monitoring the heat flow comprises a pair of sleeves attached about at least a portion of said lower ends of the sample and reference tubes, respectively, and a pair of thermocouples each connected to one of the sleeves.

10. The calorimeter of claim 1, wherein said pressure measuring means comprises a compression fitting attached to the upper end of said sample tube, and a pressure probe which extends at least partially into said heated zone.

11. A differential thermal analysis type calorimeter for performing thermal hazard testing procedures which can be utilized as an ancillary plug-in device with commercial thermal analysis data acquisition systems, and which enables simultaneous measurement of heat flow of sample reactants and direct measurement of sample pressure during a reaction, said calorimeter comprising:

- a substantially hollow furnace enclosure defining a heated zone having a top plate, and means for heating said top plate;
- a pair of longitudinally elongated heat conductive sample and reference tubes having upper and lower ends, said tubes each connected to said top plate adjacent their respective upper ends and depending downwardly therefrom within said hollow furnace enclosure, whereby said tubes are heated by said heating means and said top plate via conduction to said lower end of each tube longitudinally along said tube, said sample tube having a substantially hollow interior adjacent said lower end wherein sample reactants are received for reaction;
- a heat transfer assembly conductively attached to said heating means and said sample and reference tubes above said lower ends;
- means for directly measuring the pressure of said sample reactants within said sample tube, said pressure measuring means sealing attached adjacent the upper end of said sample tube and extending at least partially into said heated zone; and
- means for monitoring the heat flow conducted along said sample and reference tubes, respectively, during a reaction.

12. The calorimeter of claim 11, wherein said upper end of said sample tube is mounted between said top plate and said heat transfer assembly and is heated by conduction from connection to said top plate and said heat transfer assembly such that substantially no temperature gradient is produced therealong.

13. The calorimeter of claim 11, wherein said heat transfer assembly comprises oppositely disposed clamping arms to adjustably receive said sample and reference tubes in spaced relationship within said furnace enclosure.

14. The calorimeter of claim 13, wherein said clamping arms further comprise biased automatically adjustable connections for receiving said sample and reference tubes.

15. The calorimeter of claim 11, wherein said means for directly measuring the pressure of said sample reactants comprises a pressure transducer having a probe located adjacent said upper end of said sample tube within said heated zone.

16. The calorimeter of claim 11, wherein said means for monitoring the heat flow comprises a pair of sleeves attached about at least a portion of said lower ends of the sample and reference tubes, respectively, and a pair of thermocouples each connected to one of the sleeves.

17. The calorimeter of claim 11, wherein said furnace enclosure further comprises a bottom plate, and a longitudinal support post which spans between said top and bottom plates within said enclosure, and wherein said heat transfer assembly is supported along said support post.

18. The calorimeter of claim 11, wherein said pressure measuring means comprises a compression fitting attached to the upper end of said sample tube, and a pressure probe which extends at least partially into said heated zone.

19. A differential thermal analysis type calorimeter for performing thermal hazard testing procedures which can be utilized as an ancillary plug-in device with commercial thermal analysis data acquisition systems, and which enables simultaneous measurement of heat flow of sample reactants and direct measurement of sample pressure during a reaction, said calorimeter comprising:

- a substantially hollow furnace enclosure defining a heated zone having a top plate and a bottom plate, and means for heating said top plate;
- a pair of longitudinally elongated heat conductive sample and reference tubes having upper and lower ends, said tubes each connected to said top plate adjacent their respective upper ends and depending downwardly therefrom within said hollow furnace enclosure, whereby said tubes are heated by said heating means and said top plate via conduction to said lower end of each tube longitudinally along said tube, said sample tube having a substantially hollow interior adjacent said lower end wherein sample reactants are received for reaction;
- a heat transfer assembly conductively attached to said heating means and said sample and reference tubes above said lower ends;
- a longitudinal support post spanning between said top and bottom plates within said enclosure, said heat transfer assembly being supported along said support post;
- means for directly measuring the pressure of said sample reactants within said sample tube, said pressure measuring means sealingly attached adjacent the upper end of said sample tube and extending at least partially into said heated zone; and
- means for monitoring the heat flow conducted along said sample and reference tubes, respectively, during a reaction.

20. The calorimeter of claim 19, wherein said means for monitoring the heat flow comprises a pair of sleeves attached about at least a portion of said lower ends of the sample and reference tubes, respectively, and a pair of thermocouples each connected to one of the sleeves.

21. The calorimeter of claim 19, wherein said upper end of said sample tube is mounted between said top plate and said heat transfer assembly and is heated by conduction from connection to said top plate, bottom plate, support post, and said heat transfer assembly such that substantially no temperature gradient is produced therealong.

22. The calorimeter of claim 19, wherein said clamping arms further comprise biased automatically adjustable connections for receiving said sample and reference tubes.

23. The calorimeter of claim 19, wherein said pressure measuring means comprises a compression fitting attached to the upper end of said sample tube, and a pressure probe which extends at least partially into said heated zone.

* * * * *